United States Patent [19]

Chauvin et al.

[11] Patent Number: 5,502,018
[45] Date of Patent: Mar. 26, 1996

[54] NICKEL-CONTAINING COMPOSITION FOR CATALYSIS AND OLEFIN DIMERISATION AND OLIGOMERISATION PROCESS

[75] Inventors: Yves Chauvin, Rueil Malmaison, France; Sandra Einloft, Rio Grande Do Sul, Brazil; Helene Olivier, Rueil Malmaison, France

[73] Assignee: Institut Francais du Petrole, Rueil Malmaison, France

[21] Appl. No.: 309,703

[22] Filed: Sep. 21, 1994

[30] Foreign Application Priority Data

Sep. 22, 1993 [FR] France ................... 93 11382

[51] Int. Cl.⁶ .................. B01J 27/185
[52] U.S. Cl. .......... 502/213; 502/152; 502/154; 502/155; 502/162
[58] Field of Search .................. 502/152, 154, 502/155, 162, 213

[56] References Cited

U.S. PATENT DOCUMENTS 3,949,013  4/1976  Yoo et al. ................ 585/513
4,187,197  2/1980  Kabanov et al. .......... 502/117

FOREIGN PATENT DOCUMENTS 0331117  9/1989  European Pat. Off. .
0531174  3/1993  European Pat. Off. .
2220493  10/1974  France .

*Primary Examiner*—E. Rollins Cross
*Assistant Examiner*—E. D. Irzinski
*Attorney, Agent, or Firm*—Millen, White, Zelano, & Branigan

[57] ABSTRACT

The invention concerns a catalytic composition and a process for the dimerization, codimerization or oligomerization of olefins, said composition comprising a mixture of at least one bivalent nickel complex which contains two tertiary phosphine molecules, at least one nickel compound or complex compound which contains neither water nor phosphine, and at least one alkylaluminum halide. The mixture is particularly for use in ionic type non aqueous liquid compositions, such as those formed by quaternary ammonium halides and/or quaternary phosphonium halides with aluminum halides and/or alkylaluminum halides.

17 Claims, No Drawings

NICKEL-CONTAINING COMPOSITION FOR CATALYSIS AND OLEFIN DIMERISATION AND OLIGOMERISATION PROCESS

BACKGROUND OF THE INVENTION

The invention concerns a novel catalytic composition and a process for the dimerization, codimerization or oligomerization of olefins, in particular propylene. The composition comprises a mixture of at least one bivalent nickel complex containing two molecules of a tertiary phosphine, and at least one bivalent nickel compound or complex compound which does not contain phosphine. These mixtures are particularly for use in ionic liquid compositions as formed by quaternary ammonium halides and/or quaternary phosphonium halides with aluminium halides and/or alkylaluminium halides and optionally, aromatic hydrocarbons.

The nature of any substituents on the phosphorous atom of a phosphine which is bonded to nickel is known to have a considerable influence on enchainment in olefin molecules, in particular propylene, during catalytic dimerization as described by G Wilke et. al. in Ind. Eng. Chem., 1970, 62, no 12, p34, and in United Kingdom patent GB-A-1 410 430. G Wilke employed p-allyl complexes of nickel containing a single phosphine to catalyze dimerization. These complexes are difficult to prepare, relatively unstable and highly sensitive to water and to humidity. For this reason, the invention has never been put to practical use.

The phosphines were introduced into the catalyst by a variety of different methods. In particular, complexes formed by bivalent nickel salts with two equivalents of a tertiary phosphine were used in association with alkylaluminium halides as olefin dimerization catalysts, particularly for propylene. The advantage of using these complexes lies in their ease of preparation and their stability in air, also in their ease of use. The problem with these compounds is that they use two molecules of phosphine per nickel atom, and it has been shown that a single molecule is sufficient to have the desired effect. This is even more of a problem since alkylphosphines are expensive and, further, an excess of phosphine has a negative effect on the reaction rate.

SUMMARY OF THE INVENTION

We have now discovered that a mixture (preferably one equivalent) of at least one complex of bivalent nickel containing two molecules of a tertiary phosphine with (preferably one equivalent) of at least one nickel compound or complex compound which contains neither water nor phosphine and at least one alkylaluminium halide produces a stable catalyst with raised activity whose selectivity towards more branched isomers is high and equivalent to that obtained with a single complex containing two phosphines. Said catalysts are much cheaper.

More precisely, the invention provides a catalytic composition, particularly for dimerization or oligomerization of olefins, containing at least one alkylaluminium halide, at least one bivalent nickel complex containing two molecules of tertiary phosphine and at least one bivalent nickel compound or complex compound which contains neither water nor phosphine.

The invention further provides a process for the dimerization, codimerization or oligomerization of olefins, wherein at least one olefin is brought into contact with the above catalytic composition. The mixture is preferably at least partially dissolved in an ionic non aqueous medium.

The mixture of the two types of nickel compound has to be associated with an alkylaluminium halide. The mixture can be used conventionally, i.e., without a solvent, or used in the presence of a halogenated or non halogenated hydrocarbon. It can be used dissolved in an ionic non aqueous liquid composition known as a "molten salt" as resulting for example from the contact of a quaternary ammonium halide and/or quaternary phosphonium halide with an aluminium compound selected from the group formed by aluminium halides and alkylaluminium halides, for example alkylaluminium dihalides, and optionally an aluminium trihalide such as those described in U.S. Pat. No. 5 104 840.

Nickel complexes containing two phosphine molecules in accordance with the invention have general formula NiXy.2(tertiaryphosphine), wherein y is 1 or 2, and X is a sulfate anion where y is 1 and X is a chloride, bromide, iodide, nitrate or acetate where y is 2. The phosphines of the invention have general formulae $PR^1R^2R^3$ or $R^1R^2P—R'—PR^1R^2$ where $R^1$, $R^2$ and $R^3$, which may be identical or different, represent an alkyl, cycloalkyl, aryl or aralkyl radical containing 1 to 10 carbon atoms, and R' represents a bivalent aliphatic remnant containing 1 to 6 carbon atoms.

The following examples may be cited:

triisopropylphosphine, tricyclohexylphosphine, tribenzylphosphine, dicyclohexylphenylphosphine, tetracyclohexylmethylenediphosphine, diisopropyltertiobutylphosphine.

Examples of nickel complexes containing two phosphine molecules which may be used in accordance are $NiCl_2$, $2P(isopropyl)_3$ and $NiCl_2,2P(cyclohexyl)_3$.

Nickel compounds or complex compounds which do not contain phosphine are bivalent nickel salts which may be non solvated or solvated, in the absence of water, with general formula $NiX_yL_x$, wherein y is 1 or 2, and X is a sulfate ion where y is 1, and X is a chloride, bromide, iodide, nitrate or carboxylate anion where y is 2. L represents an oxygenated or nitrogenated compound such as an ether, an ester, ammonia, a primary, secondary or tertiary amine, or a heterocycle containing one or more heteroatoms which may be identical or different, and x takes the value 0, 2 or 4.

Examples of nickel compounds or complex compounds which do not contain phosphine are $NiCl_2$; $NiCl_2,2$pyridine; $NiCl_2$, dimethoxyethane; $NiCl_2,4NH_3$; nickel acetate; and nickel octoate.

Organic derivatives of aluminium in accordance with the invention have general formula $AlR_xX_{3-x}$ where R is a linear or branched alkyl radical containing 2 to 8 carbon atoms, X represents chlorine or bromine and x has a value of 1, 2 or 3. Examples are dichloroethylaluminium, ethylaluminium sesquichloride, isobutylaluminium sesquichloride, dichloroisobutylaluminium and chlorodiethylaluminium. The aluminium compound can be used, in an aluminium:nickel molar ratio of between 2:1 and 100:1, preferably between 5:1 and 50:1.

The ratio (in equivalents of Ni) between the bivalent nickel complex which contains two tertiary phosphine molecules and the bivalent nickel compound or complex compound which contains neither water nor phosphine is advantageously between 0.1 and 10, preferably between 0.8 and 2. Ratios of between 0.8 and 1.2 are preferred, more advantageously equal to or close to 1.

The compounds contained in the composition of the invention may be mixed in any order either in a hydrocarbon or halogenated hydrocarbon solvent such as chlorobenzene or methylene chloride, in the products of olefin dimerization or oligomerization, or preferably in an ionic non aqueous liquid medium.

The mixture can be formed by simple contact followed by agitation until a homogeneous liquid is produced. This is carried out in the absence of air and preferably in the presence of an olefin.

Examples of ionic non aqueous liquid media in which the reaction can be carried out are:

a) quaternary ammonium and/or quaternary phosphonium halides, in particular chlorides and/or bromides;

b) an aluminium halide and/or alkylaluminium halide (trichloride or tribromide)

c) optionally and preferably in the presence of simple, condensed or substituted aromatic hydrocarbons;

d) optionally an organic aluminium derivative.

The quaternary ammonium halides and quaternary phosphonium halides used preferably have general formulae $NR^1R^2R^3R^4X$ and $PR^1R^2R^3R^4X$, where X represents Cl or Br, $R^1, R^2, R^3$ and $R^4$ which may be identical or different each represent hydrogen or an aliphatic (saturated or unsaturated) or aromatic alkyl group containing 1 to 12 carbon atoms. The ammonium and/or phosphonium halides may also be nitrogenated or phosphorous-containing heterocyclic derivatives containing 1, 2 or 3 nitrogen and/or phosphorous atoms. Examples are tetrabutylphosphonium chloride, N-butylpyridinium chloride, ethylpyridinium bromide, 3-butyl 1-methylimidazolium chloride, diethylpyrazolium chloride, pyridinium hydrochloride and trimethylphenylammonium chloride.

Olefins which can be dimerized, codimerized or oligomerized by catalytic compositions in accordance with the invention generally contain 2 to 10 carbon atoms. They are preferably alpha olefins such as ethylene, propylene, n-butenes and n-pentenes. The olefins are alone or in a mixture, pure or diluted, for example with an alkane, as found in "cuts" from petroleum refining processes such as catalytic cracking or steam cracking.

Catalytic dimerization, codimerization or oligomerization of olefins can be carried out in a closed, semi-enclosed or continuous process with one or more reaction stages. The reaction temperature can be between −40° C. and +70° C., preferably between −20° C. and +50° C. The heat generated by the reaction can be eliminated using any method known to the skilled person. The pressure can be between atmospheric pressure or a pressure below atmospheric pressure, and 20 MPa, preferably between atmospheric pressure and 5 MPa. The reaction products and unreacted reactant(s) are separated from the catalytic system. In the preferred case where the process is carried out in an ionic non aqueous medium, the reaction products and residual reactants are separated by simple decantation then fractionated.

The following examples illustrate the invention without limiting its scope.

EXAMPLES

EXAMPLE 1

A 100 ml glass reactor, supplied with a temperature measuring means, a magnetic bar to ensure sufficient agitation and a double envelope to allow circulation of a refrigeration fluid, was purged of air and humidity and maintained at atmospheric pressure with 99% pure propylene. 22 mg (0.05 mmole) of complex $NiCl_2, 2P(iPr)_3$ and 14 mg (0.05 mmole) of compound $NiCl_2, 2$pyridine were introduced and the temperature was reduced to −15° C. 3.5 ml of a liquid composition constituted by 0.1 mole of butylmethylimidazolium chloride, 0.122 mole of sublimed aluminium chloride, 0.002 mole of dichloroethylaluminium and 0.03 mole of isodurene was introduced using a syringe. Agitation was commenced and an immediate absorption of propylene was observed. When the reactor was three quarters full of liquid, agitation was ceased, the "molten salt" was allowed to settle and a major portion of the hydrocarbon phase was extracted. This operation was repeated six times. A total of 300 g of propylene had by then been introduced. Analysis of the different fractions showed that they were composed of 75% of dimers, 22% of trimers and 3% of tetramers. The dimer composition, which was practically identical in all the fractions, comprised 81% of 2,3-dimethylbutenes, 2% of n-hexenes and 17% of 2-methylpentenes. EXAMPLE 1' (comparative)

Example 1 was repeated except that 0.1 mmole of complex $NiCl_2, 2P(iPr)3$ and no $NiCl_2 2$pyridine compound was used. The results obtained were identical except that only 240 g of propylene was converted.

EXAMPLE 2

Example 1 was repeated except that the liquid composition contained toluene instead of isodurene. Six extractions were carried out, corresponding to an introduction of 325 g of propylene. 0.2 ml of toluene was introduced following each extraction. The six fractions were constituted by 78% of dimers, 19% of trimers and 3% of tetramers. The dimers contained 83% of 2,3-dimethylbutenes, 2% of n-hexenes and 15% of 2-methylpentenes.

EXAMPLE 3

Example 1 was repeated except that, instead of the $NiCl_2, 2p(iPr)_3$ complex, the same quantity of $NiCl_2, 2p(Bu)_3$ complex was used and the operating temperature was +5° C. When the reactor was three quarters full of liquid, agitation was ceased, the "molten salt" was allowed to settle and a major portion of the hydrocarbon phase was extracted. This operation was repeated seven times. A total of 408 g of propylene had been introduced by then. Analysis of the different fractions showed that they were composed of 89% of dimers, 8% of trimers and 3% of tetramers. The dimer composition, which was practically identical in all the fractions, comprised 31% of 2,3-dimethylbutenes, 5% of n-hexenes and 64% of 2-methylpentenes.

We claim:

1. A catalytic composition comprising a mixture of at least one alkylaluminum halide, at least one bivalent nickel complex which contains two molecules of tertiary phosphine and at least one bivalent nickel compound or complex compound containing neither water nor phosphine.

2. A catalytic composition according to claim 1 wherein the aluminium:nickel molar ratio is between 2:1 and 100:1.

3. A catalytic composition according to claim 1 wherein the nickel complex which contains two phosphine molecules has general formula $NiX_y.2$(tertiary phosphine), in which y is 1 or 2, and X is a sulfate anion where y is 1 and a chloride, bromide, iodide, nitrate or acetate anion where y is 2.

4. A catalytic composition according to claim 3 wherein the tertiary phosphine is triisopropylphosphine, tricyclohexylphosphine, tribenzylphosphine, dicyclohexylphenylphosphine, tetracyclohexylmethylenediphosphine or diisopropyltertiobutylphosphine.

5. A catalytic composition according to claim 1 wherein the complex which contains phosphine is NiCl$_2$,2P(isopropyl)$_3$ or NiCl$_2$,2P(cyclohexyl)$_3$.

6. A catalytic composition according to claim 1 wherein the nickel compound which does not contain phosphine has general formula NiX$_y$L$_x$, where y is 1 or 2, and x is a sulfate anion where y is 1 and a chloride, bromide, iodide, nitrate or acetate anion where y is 2, L represents an oxygenated or nitrogenated compound and x takes the value 0, 2 or 4.

7. A catalytic composition according to claim 5 wherein the nickel compound or complex compound which does not contain phosphine is NiCl$_2$; NiCl$_2$,2pyridine; NiCl$_2$, dimethoxyethane; NiCl$_2$,4NH$_3$; nickel acetate or nickel octoate.

8. A catalytic composition according to claim 1 wherein the alkyl aluminum halide is dichloroethylaluminium, dichloroisobutylaluminium, chlorodiethylaluminium, ethylaluminium sesquichloride or diisobutylaluminium sesquichloride.

9. A catalytic composition according to claim 1 wherein the ratio (in equivalents of Ni) between the bivalent nickel complex containing two tertiary phosphine molecules and the bivalent nickel compound or complex compound which contains neither water nor phosphine is between 0.1 and 10.

10. A catalytic composition according to claim 6 wherein the ratio (in equivalents of Ni) between the bivalent nickel complex containing two tertiary phosphine molecules and the bivalent nickel compound or complex compound which contains neither water nor phosphine is between 0.8 and 2.

11. A catalytic composition according to claim 7 wherein the ratio (in equivalents of Ni) between the bivalent nickel complex containing two tertiary phosphine molecules and the bivalent nickel compound or complex compound which contains neither water nor phosphine is between 0.8 and 1.2.

12. A catalytic composition according to claim 1 wherein the ratio (in equivalents of Ni) between the bivalent nickel complex containing,, two tertiary phosphine molecules and the bivalent nickel compound or complex compound which contains neither water nor phosphine is equal to 1.

13. A catalytic composition according to claim 1 in which said mixture is dissolved, at least in part, in an ionic non-aqueous medium.

14. A catalytic composition according to claim 1 in which said mixture is dissolved, at least in part, in an ionic non-aqueous medium comprising at least one quaternary ammonium halide and/or one quaternary phosphonium halide, and at least one aluminum compound which is an alkylaluminum halide or an aluminum halide.

15. A catalytic composition according to claim 1 obtained by mixing of at least one bivalent nickel complex containing two molecules of tertiary phosphine with at least one bivalent nickel compound or complex compound containing neither water not phosphine, then mixing with at least one alkylaluminum halide.

16. A catalytic composition according to claim 13 containing an aromatic hydrocarbon.

17. A catalytic composition according to claim 6, wherein the oxygenated or nitrogenated compound is an ether, an ester, ammonia, a primary, secondary or tertiary amine, or a heterocycle containing one or more heteroatoms which may be identical of different.

* * * * *